United States Patent
Musitano

(10) Patent No.: US 9,707,197 B2
(45) Date of Patent: Jul. 18, 2017

(54) TOPICAL COMPOSITION FOR PAIN RELIEF

(71) Applicant: Patrick Musitano, Hamilton (CA)

(72) Inventor: Patrick Musitano, Hamilton (CA)

(73) Assignee: Multimode Medical Inc., Hamilton (CA)

( * ) Notice: Subject to any disclaimer, the term of this patent is extended or adjusted under 35 U.S.C. 154(b) by 0 days.

(21) Appl. No.: 15/249,978

(22) Filed: Aug. 29, 2016

(65) Prior Publication Data
US 2016/0367508 A1    Dec. 22, 2016

Related U.S. Application Data

(63) Continuation of application No. 14/872,581, filed on Oct. 1, 2015, now abandoned.

(60) Provisional application No. 62/058,231, filed on Oct. 1, 2014.

(51) Int. Cl.
| | |
|---|---|
| *A61K 31/197* | (2006.01) |
| *A61K 9/00* | (2006.01) |
| *A61K 31/135* | (2006.01) |
| *A61K 31/167* | (2006.01) |
| *A61K 31/192* | (2006.01) |
| *A61K 47/10* | (2017.01) |
| *A61K 47/14* | (2017.01) |
| *A61K 47/24* | (2006.01) |

(52) U.S. Cl.
CPC .......... *A61K 31/197* (2013.01); *A61K 9/0014* (2013.01); *A61K 31/135* (2013.01); *A61K 31/167* (2013.01); *A61K 31/192* (2013.01); *A61K 47/10* (2013.01); *A61K 47/14* (2013.01); *A61K 47/24* (2013.01)

(58) Field of Classification Search
CPC .................................................. A61K 31/197
USPC ....................................................... 514/567
See application file for complete search history.

(56) References Cited

U.S. PATENT DOCUMENTS

2016/0095832 A1    4/2016    Musitano et al.

OTHER PUBLICATIONS

[No Author Listed] Technical Report: PCCA Lipoderm® Delivers Four Drugs Simultaneously in Transdermal Study. Sep. 21, 2011. 2 pages. Accessed Sep. 28, 2015 via http://www.pccarx.com/about-pcca/pcca-studies/studies/item/93-pcca-lipoderm-and-four-drugs-transdermal-study.

Arnold et al., The Release and Transdermal Penetration of Baclofen Formulated in Poloxamer Lecithin Organogel. International Journal of Pharmaceutical Compounding. Nov./Dec. 2009. 13(6): 569-71.
Barton et al., A double-blind, placebo-controlled trial of a topical treatment for chemotherapy-induced peripheral neuropathy: NCCTG trial N06CA. Support Care Cancer. Jun. 2011 19(6): 83341. Published online May 25, 2010. DOI: 10.1007/s00520-010-0911-0.
Baumann et al., Safety and efficacy of a rapid-acting topical 4% lidocaine gel in a unique drug delivery system. J Drugs Dermatol. Dec. 2010. 9(12): 1500-4. Abstract Only.
Burch et al., Lidocaine patch 5% improves pain, stiffness, and physical function in osteoarthritis pain patients. Osteoarthritis and Cartilage. Mar. 2004. 12 (3): 253-5.
Derry et al., Topical lidocaine for neuropathic pain in adults. Cochrane Pain, Palliative and Supportive Care Group. Jul. 1, 2014. 3 pages. Published online Jul. 24, 2014. Accessed Sep. 28, 2015. DOI: 10.1002/14651858/CD010958.pub2 Abstract.
Gerner et al., Topical amitriptyline in healthy volunteers. Reg Anesth Pain Med. Jul.-Aug. 2003 28(4): 289-93. Abstract.
Haderer et al, Cutaneous Analgesia After Transdermal Application of Amitriptyline Versus Lidocaine in Rats. Anesthesia & Analgesia. Pain Medicine: Research Report. Jun. 2003. 96(6): 1707-10. DOI: 10.1213/01.ANE.0000060456.91215.90.
Keservani et al., Novel Vesicular Approach for Topical Delivery of Baclofen Via Niosomes. Latin America Journal of Pharmacy. Mar. 8, 2010. 29(8): 1364-70. Retrieved Jul. 9, 2015.
Kopsky et al., High Doses of Topical Amitriptyline in Neuropathic Pain: Two Cases and Literature Review. Clinical Review. Pain Practice. 2012. 12(2):148-53.
Paudel et al, Challenges and opportunities in dermal/transdermal delivery. Ther. Delivery. Jul. 2010. 1(1):109-31. Author Manuscript. Available in PMC May 1, 2011. Accessed Sep. 28, 2015.
Rhee, Transdermal delivery of ketoprofen using microemulsions. International Journal of Pharmaceuticals. Mar. 14, 2001. 228: 161-70.
Sawynok. Topical and Peripherally Acting Analgesics. Pharmacological Reviews. Pharmacol Review. 2003. 55: 1-20.
Scheinfeld Topical treatments of skin pain: a general review with a focus on hidradenitis suppurativa with topical agents. Dermatology Online Journal. Jul. 2014. 20(7). 19 pages.
Schreiber et al., Diabetic neuropathic pain: Physiopathology and treatment. World Journal of Diabetes. Apr. 15, 2015. 6(3): 432-44. DOI: 10.4239/wjd.v6.i3.432. Accessed Sep. 28, 2015.
Sekiya et al, Ketoprofen Absorption by Muscle and Tendon after Topical or Oral Administration in Patients Undergoing Anterior Cruciate Ligament Reconstruction. AAPS PhamSciTech. Mar. 2010. 11(1): 154-8. Published online Jan. 20, 2010. DOI: 10.1208/s12249-009-9367-2.
Valenta et al., In Vitro Diffusion Studies of Ketoprofen Transdermal Therapeutic Systems. Drug Development and Industrial Pharmacy. 1995. 21(15): 1799-1805. Accessed Jul. 10, 2015.
Zeltzer, The Use of Topical Analgesics in Treatment of Neuropathic Pain: Mechanism of Action, Clinical Efficacy, and Psychologic. Medscape Neurology. Jul. 1, 2004. 7 pages. Accessed Jul. 29, 2015.

*Primary Examiner* — Taofiq A Solola
(74) *Attorney, Agent, or Firm* — Wolf, Greenfield & Sacks, P.C.

(57) ABSTRACT

The composition comprises 0.5% to 10% by weight of a neuropathic analgesic; 0.5% to 10% by weight of a muscle relaxant; 0.5% to 20% by weight of an anti-inflammatory analgesic; and 0.5% to 10% by weight of an anesthetic.

3 Claims, No Drawings

TOPICAL COMPOSITION FOR PAIN RELIEF

RELATED APPLICATIONS

This application is a continuation of U.S. patent application Ser. No. 14/872,581, filed Oct. 1, 2015, entitled "Topical Composition for Pain Relief," which claims the benefit of U.S. Provisional Patent Application Ser. No. 62/058,231, filed Oct. 1, 2014, entitled "Topical Composition for Pain Relief," each of which is incorporated herein by reference in its entirety for all purposes.

FIELD OF THE INVENTION

The present invention relates to the field of pain treatment.

BACKGROUND

Many people suffer from musculoskeletal conditions such as soft tissue trauma and arthritis. Some bear the pain associated with those conditions for prolonged periods. Treatment of musculoskeletal pain using anti-inflammatory drugs, such as non-steroidal anti-inflammatory drugs or NSAIDs, is not always effective.

SUMMARY OF THE INVENTION

Forming one aspect of the invention is a composition comprising, by weight:
  0.5% to 10% neuropathic analgesic;
  0.5% to 10% muscle relaxant;
  0.5% to 10% by weight of an anesthetic; and
  0.5% to 20% anti-inflammatory analgesic.

Forming another aspect of the invention, the neuropathic analgesic can be Amitriptyline, the muscle relaxant can be Baclofen, the anesthetic can be Lidocaine and the anti-inflammatory analgesic can be Ketoprofen.

Forming another aspect of the invention is a topical composition comprising, by weight:
  approximately 2% Amitriptyline;
  approximately 5% Baclofen;
  approximately 10% Ketoprofen; and
  approximately 5% Lidocaine Further aspects of the invention will become apparent from the following description.

DETAILED DESCRIPTION

An exemplary embodiment of the invention is a composition comprising:
  approximately 2% Amitriptyline;
  approximately 5% Baclofen;
  approximately 10% Ketoprofen;
  approximately 5% Lidocaine;
  approximately 2% ethyl alcohol;
  approximately 6% ethoxy diglycol;
  approximately 15.47% an oil phase; and
  approximately 54.53% poloxamer 20% gel phase.

The oil phase is produced by mixing 50 parts granular soya lecithin, 50 parts isopropyl palmitate (USP-NF), and 1.3 parts sorbic acid (USP-NF) powder. The mixture is allowed to sit until a syrup that looks similar to motor oil is produced, which process takes a few hours.

The poloxamer 20% gel phase is produced by mixing 20 grams poloxamer 407, 0.3 grams potassium sorbate and 79.7 ml purified cold water, and allowing the resulting mixture to stand for approximately 24 hours in cold conditions, such as in a refrigerator.

Experimental Results

It has been found that the composition can be used to treat musculoskeletal inflammation and/or pain resulting from various types of musculoskeletal conditions. For example, the composition can be used to treat soft tissue trauma pain and/or inflammation, arthritis, post-operative pain (e.g., resulting from scarring) and/or stiffness, neuropathic pain, joint pain, tendonitis, osteoarthritis, dermatomal pain, knee pain, hip pain, back pain, shoulder pain, wrist pain, neck pain, arm pain, ankle pain, sciatic pain, chronic pain, acute pain, or inflammation. In general, the clinical situations where the product has been found useful include patients who are waiting a long time for surgery as a result of long waiting lists. It is also useful in patients for whom surgery is contraindicated (advanced age, poor health etc). It has been found useful in the setting of acute pain following injury or exacerbation of underlying arthritis, in the management of post-operative pain and chronic pain and in the management of post-operative stiffness after total knee replacement by enabling more aggressive physiotherapy. In a survey of 60 patients using the product, 80% reported some form of relief. Of those who experienced relief, the average pain relief they reported was 67%. The only side effect reported was a rash in 3% of the patients surveyed. The rash resolved when they discontinued use.

For use, the composition is typically rubbed onto the skin in the areas of pain and/or inflammation, two to three times daily.

What follows is a random selection of exemplary results:
Patient 1
A 50 year old man with mild to moderate osteoarthritis of the knee had tried physiotherapy and bracing, with oral NSAIDs as needed. After six weeks of use of the cream, he reported significant pain relief and as a result, required less oral medication.
Patient 2
A 65 year old man with left hip arthritis pain and low back pain reported significant pain relief after using the cream. As a result, he decided to postpone a total hip replacement.
Patient 3
A 55 year old woman with osteoarthritis of the knee used viscosupplementation injections in conjunction with the cream, and as a result, reported significant pain reduction.
Patient 4
A 45 year old woman with greater trochanteric bursitis of the hip reported significant pain relief after using the cream.

Whereas only a single embodiment is hereby described in detail, variations are possible. Accordingly, the invention should be understood to be limited only by the accompanying claims, purposively construed.

The invention claimed is:
1. A topical composition comprising, by weight:
  0.5% to 10% neuropathic analgesic;
  0.5% to 10% muscle relaxant;
  0.5% to 10% by weight of an anesthetic; and
  0.5% to 20% anti-inflammatory analgesic.
2. The composition according to claim 1, wherein the neuropathic analgesic is Amitriptyline, the muscle relaxant is Balcofen, the anesthetic is Lidocaine and the anti-inflammatory analgesic is Ketoprofen.
3. A topical composition comprising, by weight:
  approximately 2% Amitriptyline;
  approximately 5% Baclofen;
  approximately 10% Ketoprofen; and
  approximately 5% Lidocaine.

* * * * *

UNITED STATES PATENT AND TRADEMARK OFFICE
CERTIFICATE OF CORRECTION

| | | |
|---|---|---|
| PATENT NO. | : 9,707,197 B2 | Page 1 of 1 |
| APPLICATION NO. | : 15/249978 | |
| DATED | : July 18, 2017 | |
| INVENTOR(S) | : Patrick Musitano | |

It is certified that error appears in the above-identified patent and that said Letters Patent is hereby corrected as shown below:

On the Title Page

Item (71) should read:
(71) Applicant: Multimode Medical Inc., Hamilton (CA)

Signed and Sealed this
Thirty-first Day of October, 2017

Joseph Matal
*Performing the Functions and Duties of the
Under Secretary of Commerce for Intellectual Property and
Director of the United States Patent and Trademark Office*